US00PP22017P2

(12) United States Plant Patent
Heuger

(10) Patent No.: US PP22,017 P2
(45) Date of Patent: Jul. 5, 2011

(54) ***HELLEBORUS* PLANT NAMED 'HLR 150'**

(50) Latin Name: ***Helleborus orientalis* hybrid**
Varietal Denomination: HLR 150

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 12/798,343

(22) Filed: Mar. 31, 2010

(51) Int. Cl.
*A01H 5/00* (2006.01)

(52) U.S. Cl. ..... Plt./439

(58) Field of Classification Search ..... Plt./439
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'HLR 150', characterized by its upright and outwardly arching plant habit; uniform flowering habit; long flowering period; single light pink-colored flowers with red purple-colored central spots; and good garden performance.

2 Drawing Sheets

Botanical designation: *Helleborus orientalis* hybrid.
Cultivar denomination: 'HLR 150'.

BACKGROUND OF THE INVENTION

The present invention relates to a new and distinct cultivar of *Helleborus* plant, botanically known as *Helleborus orientalis* hybrid, and hereinafter referred to by the name 'HLR 150'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in November, 2002 of two unnamed proprietary seedling selections of *Helleborus* orientalis hybrid, not patented. The new *Helleborus* plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'HLR 150'. These characteristics in combination distinguish 'HLR 150' as a new and distinct cultivar of *Helleborus* plant:

1. Upright and outwardly arching plant habit.
2. Uniform flowering habit.
3. Long flowering period.

4. Single light pink-colored flowers with red purple-colored central spots.
5. Good garden performance.

Compared to plants of the parent selections, plants of the new *Helleborus* flower more freely and more uniformly.

Plants of the new *Helleborus* can be compared to plants of *Helleborus orientalis* hybrid 'HGC Merlin', disclosed in U.S. Plant Pat. No. 15,705. Plants of the new *Helleborus* differ primarily from plants of 'HGC Merlin' in the following characteristics:

1. Plants of the new *Helleborus* have larger flowers than plants of 'HGC Merlin'.
2. Flowers of plants of the new *Helleborus* are light pink in color with red purple-colored central spots whereas flowers of plants of 'HGC Merlin' are dark purple in color.

BRIEF DESCRIPTION OF THE PHOTOGRAPHS

The accompanying colored photographs illustrate the overall appearance of the new *Helleborus* plant, showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'HLR 150' grown in a container.

The photograph on the second sheet is a close-up view of a typical flower of 'HLR 150'.

DETAILED BOTANICAL DESCRIPTION

The aforementioned photographs and following observations, measurements and values describe plants grown in Glandorf, Germany in 1.5-liter containers during the winter in a glass-covered greenhouse and under conditions which closely approximate commercial *Helleborus* production. During the production of the plants, day temperatures ranged from 12° C. to 32° C. and night temperatures ranged from 3° C. to 18° C. Plants were one year old when the photographs and the description were taken. In the following description, color references are made to The Royal Horticultural Society Colour Chart, 2007 Edition, except where general terms of ordinary dictionary significance are used.

Botanical classification: *Helleborus orientalis* hybrid 'HLR 150'.

Parentage:

*Female, or seed, parent.*—Unnamed proprietary seedling selection of *Helleborus orientalis* hybrid, not patented.

*Male, or pollen, parent.*—Unnamed proprietary seedling selection of *Helleborus orientalis* hybrid, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and outwardly arching plant habit; shape, globular to broad inverted triangular; moderately vigorous growth habit.

*Plant height.*—About 34.8 cm.

*Plant diameter* (*area of spread*).—About 33.7 cm.

Foliage description:

*Arrangement.*—Leaves arranged in a basal rosette; palmately compound with five leaflets per leaf.

*Leaf length.*—About 16.2 cm.

*Leaf width.*—About 21.4 cm.

*Leaflet length.*—About 12.5 cm.

*Leaflet width.*—About 4.4 cm.

*Leaf shape.*—Palmate; orbicular in outline.

*Leaflet shape.*—Elliptic to narrowly obovate; lowest leaflets typically cleft.

*Leaflet apex.*—Acute.

*Leaflet base.*—Attenuate.

*Leaflet margin.*—Serrate.

*Leaflet texture, upper and lower surfaces.*—Smooth, glabrous; leathery.

*Leaflet venation pattern.*—Pinnate.

*Leaflet color.*—Developing leaves, upper surface: Close to 143A. Developing leaves, lower surface: Close to 144A. Fully developed leaves, upper surface: Between N137D and 147A; venation, close to 144A to 144B. Fully developed leaves, lower surface: Close to 147B; venation, close to 144B to 144C.

*Petiole.*—Length: About 12.5 cm. Diameter: About 5 mm. Texture, upper and lower surfaces: Smooth, glabrous. Color, upper and lower surfaces: Close to 143C to 144B.

Flower description:

*Flower shape and habit.*—Single rotate flowers; uniform flowering habit; about five flowers per terminal cyme; flowers facing outwardly to nodding.

*Fragrance.*—None detected.

*Natural flowering season.*—Long flowering period; plants flower from winter to early spring in Germany.

*Flower longevity on the plant.*—About ten days; flowers not persistent.

*Flower buds.*—Length: About 2.8 cm. Diameter: About 1.5 cm. Shape: Ovate. Color: Close to 157A to 157B slightly flushed with close to 182D; towards the base, close to 143B to 143C.

*Inflorescence height.*—About 34.8 cm.

*Inflorescence diameter.*—About 15.5 cm.

*Flower diameter.*—About 8.8 cm.

*Flower depth* (*height*).—About 2.9 cm.

*Petals.*—Transformed into nectaries.

*Sepals.*—Arrangement: About five in a single whorl. Length: About 4.8 cm. Width: About 3.7 cm. Shape: Broadly ovate. Apex: Broadly acute. Margin: Entire. Texture, upper and lower surfaces: Smooth, glabrous. Color: When opening, upper surface: Close to 157C; central spots, close to 187B to 187C; towards the base, close to 145A to 145B. When opening, lower surface: Close to 157C; towards the base, close to 144B. Fully opened, upper surface: Close to 75B to 75D; central spots, close to N186C and 187A; towards the base, close to 145C to 145D. Fully opened, lower surface: Close to 75A to 75B and 186C to 186D; at the base, close to 143C.

*Peduncles.*—Strength: Moderately strong. Length: About 30.5 cm. Diameter: About 7 mm. Aspect: About 15° from vertical. Texture: Smooth, glabrous. Color: Close to 144C to 144D.

*Pedicels.*—Strength: Moderately strong. Length: About 3.2 cm. Diameter: About 2 mm. Aspect: About 25° from the peduncle axis. Texture: Smooth, glabrous. Color: Close to 144C.

*Reproductive organs.*—Stamens: Quantity per flower: About 90. Filament length: About 1.3 cm. Filament color: Close to 157D. Anther shape: Narrowly reniform. Anther length: About 3 mm. Anther color: Close to 155A. Pollen amount: Moderate. Pollen color: Close to 158D. Pistils: Quantity per flower: About five. Pistil length: About 1.4 cm. Stigma shape: Club-shaped. Stigma color: Close to 145D. Style length: About 1.3 cm. Style color: Close to 145D. Ovary color: Close to 145B to 145C. Nectaries (transformed petals): Quantity per flower: About eleven. Length: About 9 mm. Diameter, apex: Close to 5 mm. Diameter, base: Close to 1 mm. Shape: Flattened triangular. Color: Close to 144A to 144B; towards the apex, close to N144A.

*Seeds/fruits.*—Seed and fruit development have not been observed.

Garden performance: Plants of the new *Helleborus* have been observed to have good garden performance and to tolerate rain, wind and temperatures ranging from about −10° C. to about 35° C.

Pathogen/pest resistance: Plants of the new *Helleborus* have not been shown to be resistant to pathogens and pests common to *Helleborus*.

It is claimed:

1. A new and distinct *Helleborus* plant named 'HLR 150' as illustrated and described.

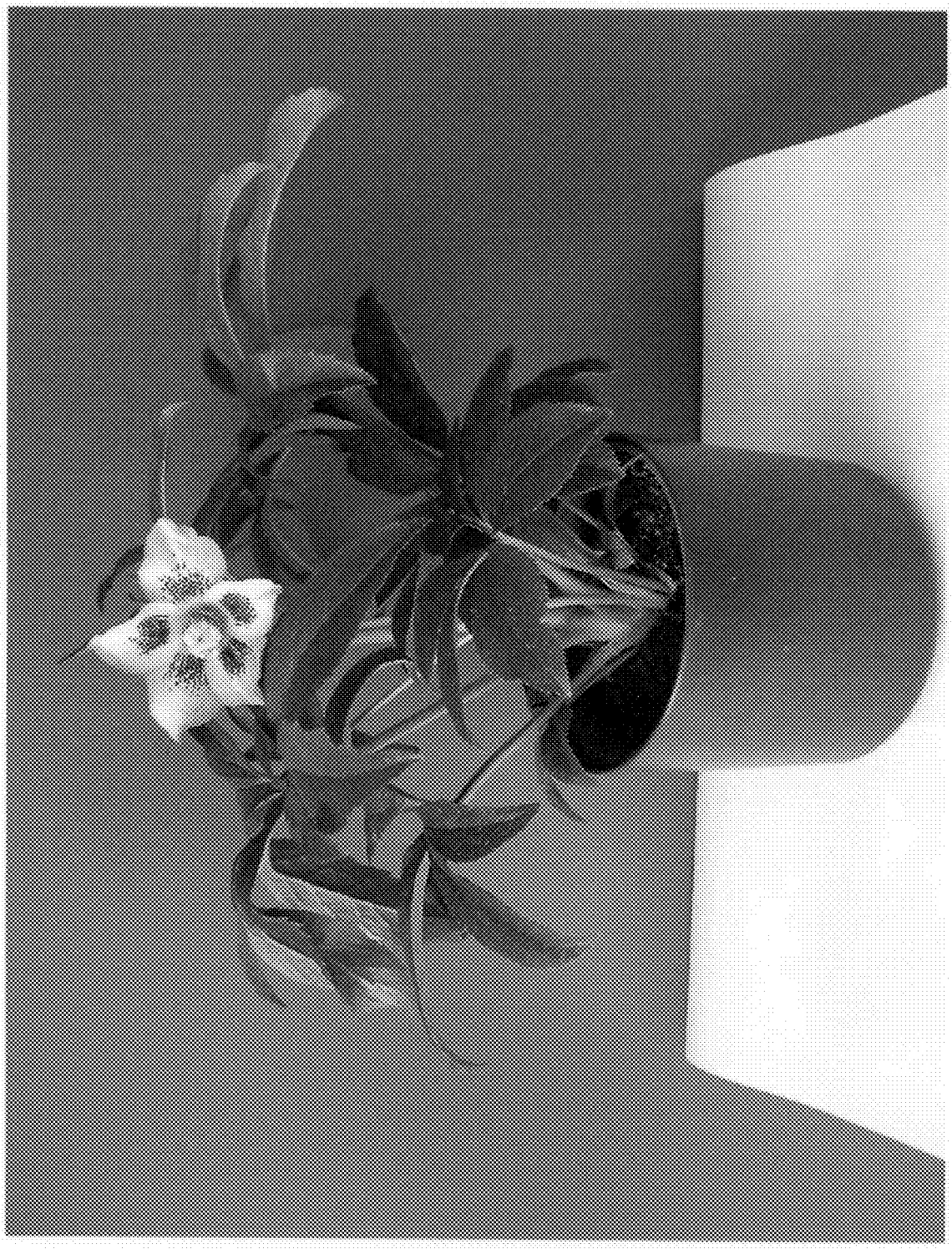

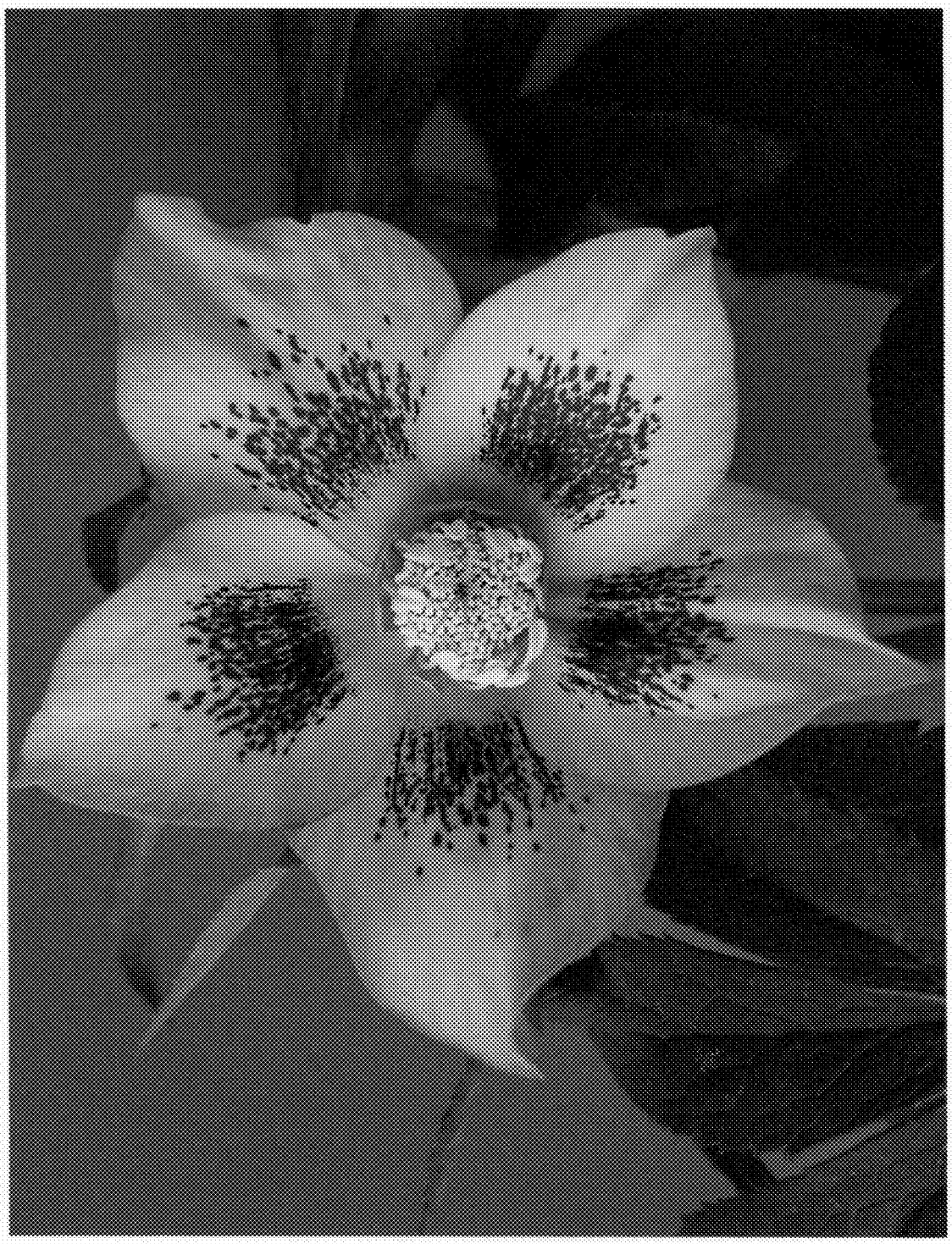

* * * * *